(12) United States Patent
O'Hara (10) Patent No.: US 7,876,883 B2
(45) Date of Patent: Jan. 25, 2011

(54) MAMMOGRAPHY X-RAY HOMOGENIZING OPTIC

(76) Inventor: David O'Hara, 4356 David Ct., Tallahassee, FL (US) 32309

( * ) Notice: Subject to any disclaimer, the term of this patent is extended or adjusted under 35 U.S.C. 154(b) by 14 days.

(21) Appl. No.: 12/384,936

(22) Filed: Apr. 10, 2009

(65) Prior Publication Data
US 2009/0257562 A1 Oct. 15, 2009

Related U.S. Application Data

(60) Provisional application No. 61/123,784, filed on Apr. 10, 2008.

(51) Int. Cl.
*H01J 35/14* (2006.01)
*H01J 35/08* (2006.01)
*H01J 35/02* (2006.01)
*H01J 35/00* (2006.01)

(52) U.S. Cl. ........................... 378/121; 378/143

(58) Field of Classification Search .......... 378/121, 378/143, 210; 250/368; 385/34, 40, 133
See application file for complete search history.

(56) References Cited
U.S. PATENT DOCUMENTS
1,596,405 A * 8/1926 Dechend .................. 378/121
2,677,069 A * 4/1954 Bachman .................. 378/121
3,584,219 A * 6/1971 Herglotz et al. ............. 250/399
5,157,704 A * 10/1992 Harding ................... 378/119
5,828,505 A * 10/1998 Farmiga ................... 359/857
6,993,115 B2 * 1/2006 McGuire et al. ............ 378/124
2005/0135766 A1* 6/2005 Cianciotto et al. ........... 385/133
2007/0242924 A1* 10/2007 Cianciotto et al. ........... 385/133

* cited by examiner

*Primary Examiner*—Edward J Glick
*Assistant Examiner*—Anastasia Midkiff
(74) *Attorney, Agent, or Firm*—J. Wiley Horton (57) ABSTRACT

A conical anode X-ray source with a spot size approximately one tenth of the size of existing mammography devices. The source produces the same or higher radiance than the prior art. It also produces almost no high-energy Bremstrahlung. The electron beam is directed into a conical anode so that it strikes the reflecting surface at an angle which produces total internal reflection. The X-rays emitted via the reflection would ordinarily exit the small end of the conical anode in a diverging conical pattern—producing an undesirable "ring" configuration at the image plane. A homogenizing optic is therefore preferably added to the small end of the conical anode. The homogenizing optic is sized to reflect the X-rays emerging from the conical anode and thereby create a uniform "spot" source at the far end of the homogenizing optic.

13 Claims, 6 Drawing Sheets

MAMMOGRAPHY X-RAY HOMOGENIZING OPTIC

CROSS-REFERENCES TO RELATED APPLICATIONS

This application is a non-provisional application claiming the benefit pursuant to 37 C.F.R. §1.53 (c) of an earlier-filed provisional application. The provisional application was filed on Apr. 10, 2008 and was assigned Ser. No. 61/123,784. It listed the same inventor.

STATEMENT REGARDING FEDERALLY SPONSORED RESEARCH OR DEVELOPMENT

Not Applicable.

MICROFICHE APPENDIX

Not Applicable

BACKGROUND

1. Field of the Invention

This invention relates to the field of X-ray machines. More specifically, the invention comprises a conical anode X-ray source with an aligned homogenizing optic.

2. Background of the Invention

Figure 1:
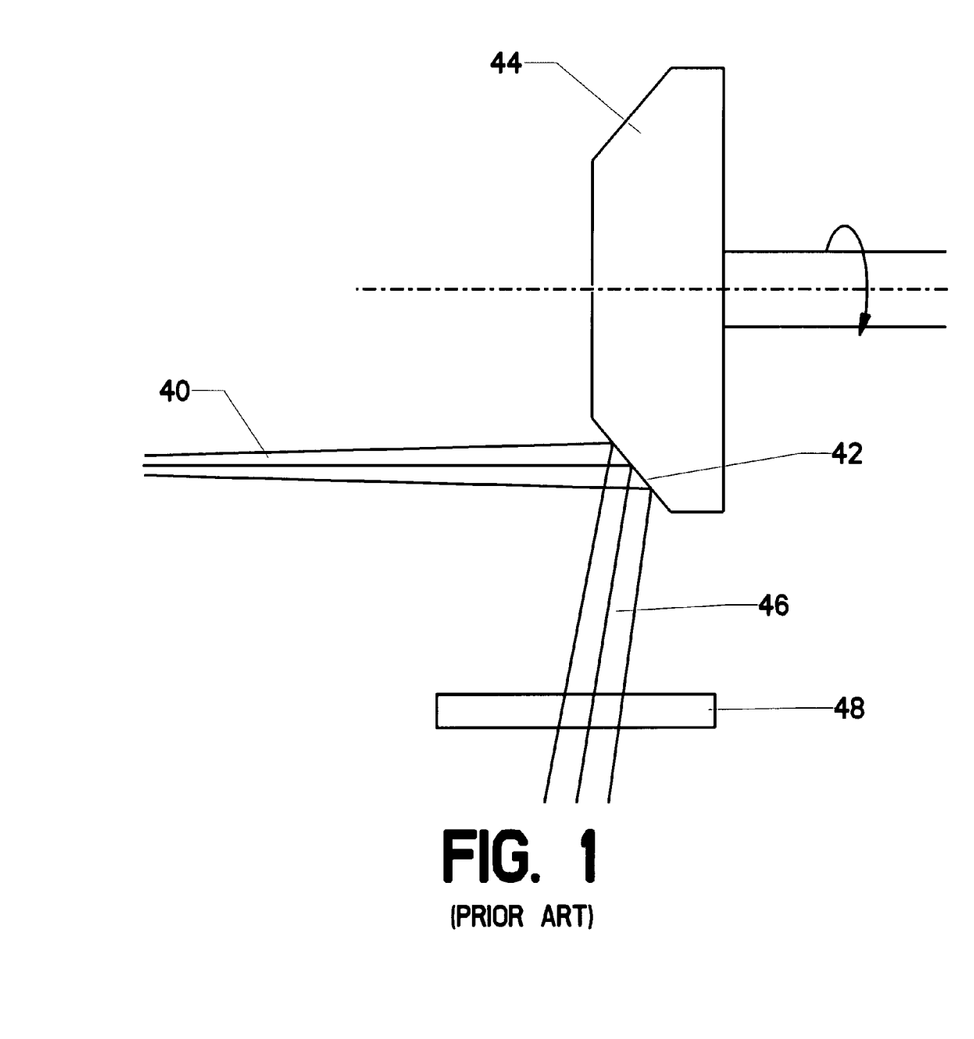
FIG. 1 is an elevation view, showing simplified depiction of a prior art X-ray tube.

FIG. 1 shows a traditional X-ray generating device. Electron beam 40 is focused on reflecting surface 42 of rotating anode 44. X-rays are generated by the electron beam striking the surface. These reflect laterally as X-ray beam 46, which are emitted from the machine through side window 48. The prior art anode is rotated to prevent overheating, since the electron beam would cause local overheating if it remained focused on one spot of the anode.

Although the present invention has applications in many fields, it is particularly well-suited to the field of mammography. Accordingly, the reader may wish to know some of the constraints particular to this field. Mammography requires very high resolution radiographs in order to provide the details needed for diagnostic work. However, because a-patient typically undergoes screening mammograms on numerous occasions, it is important to keep the dosage as low as possible.

Spatial resolution requirements suggest that a small source of X-ray emissions would be best. However, it is difficult to make and X-ray source that is sufficiently small yet powerful enough to provide ultra-high resolution in the resulting image. Known sources also produce too much high-energy radiation, which produces background contrast problems. The apparent spot size is also not constant across the image plane. The spot size also tends to change over the time so the instruments must frequently be recalibrated.

Radiography of soft tissue is normally done with lower X-ray energy than dense tissue or bone. The preferred energy range for mammography is about 17-25 KeV. The soft tissue features show better contrast using low energy X-rays. Higher energy ("harder") X-rays simply produce more background due to scatter. The potential used to produce the desired molybdenum "K" line of X-rays is about 17.5 KV X-ray tube potential. The production of X-ray lines is proportional to the overvoltage of the X-ray tube, according to the following expression:

$I_K \propto i(V-V_K)$, where $I_K$ is the intensity of the characteristic molybdenum K line, i is the tube current, $V_K$ is the minimum potential necessary to produce the Mo(K) line (17.5 KV), and V is the actual tube potential.

Tubes for mammography are normally operated at about 26 KV to minimize the high energy Bremstrahlung ("braking radiation") that causes background problems. A molybdenum filter is sometimes used to minimize the high energy Bremstrahlung while still passing the desired Mo(K) line, but this also suppresses some of the desired emissions. If the production of Bremstrahlung could be minimized, then the electrical potential of the tube could be raised and the intensity of the desired line radiation could thereby be increased.

For example, if $V_K$ is 17.5 KV, once may easily see from the expression $I_K \propto i(V-V_K)$ that raising V from 26 KV to 50 KV would increase the intensity of the desired line radiation by a factor of about 9. Ordinarily this increase would produce a substantial increase in Bremstrahlung, largely if not completely eliminating any gain in image resolution. The reader will therefore appreciate that an X-ray optic able to increase the intensity of the desired line radiation without producing a related increase in Bremstrahlung, would be highly desirable. The present invention proposes just such a device. The present invention also substantially improves the uniformity of the desired emissions.

BRIEF SUMMARY OF THE INVENTION

The present invention is a conical anode X-ray source with a spot size approximately one tenth of the size of existing mammography devices. The source produces the same or higher radiance than the prior art. It also produces almost no high-energy Bremstrahlung. The spot size is uniform across the image plane and it does not vary over time. With this new source, it is possible to provide extremely high resolution while retaining an acceptable patient dose level.

The electron beam is directed into the conical anode so that it strikes the reflecting surface at an angle which produces total internal reflection. The X-rays emitted via the reflection would ordinarily exit the small end of the conical anode in a diverging conical pattern—producing an undesirable "ring" configuration at the image plane. A homogenizing optic is therefore preferably added to the small end of the conical anode. The homogenizing optic is sized to reflect the X-rays emerging from the conical anode and thereby create a uniform "spot" source at the far end of the homogenizing optic.

Referance Numerals Used

| | | | |
|---|---|---|---|
| 10 | X-ray source | 12 | conical anode |
| 14 | first filter | 16 | homogenizing optic |
| 18 | second filter | 20 | central axis |
| 22 | reflecting surface | 24 | incident ray |
| 26 | reflected ray | 28 | low energy incident ray |
| 30 | low energy reflected ray | 32 | high energy incident ray |
| 34 | electron ray | 36 | reflected X-ray |
| 38 | ring projection | 40 | electron beam |
| 42 | reflecting surface | 44 | rotating anode |
| 46 | X-ray beam | 48 | side window |
| 50 | female conical reflecting surface | | |

DETAILED DESCRIPTION OF THE INVENTION

Figure 2:
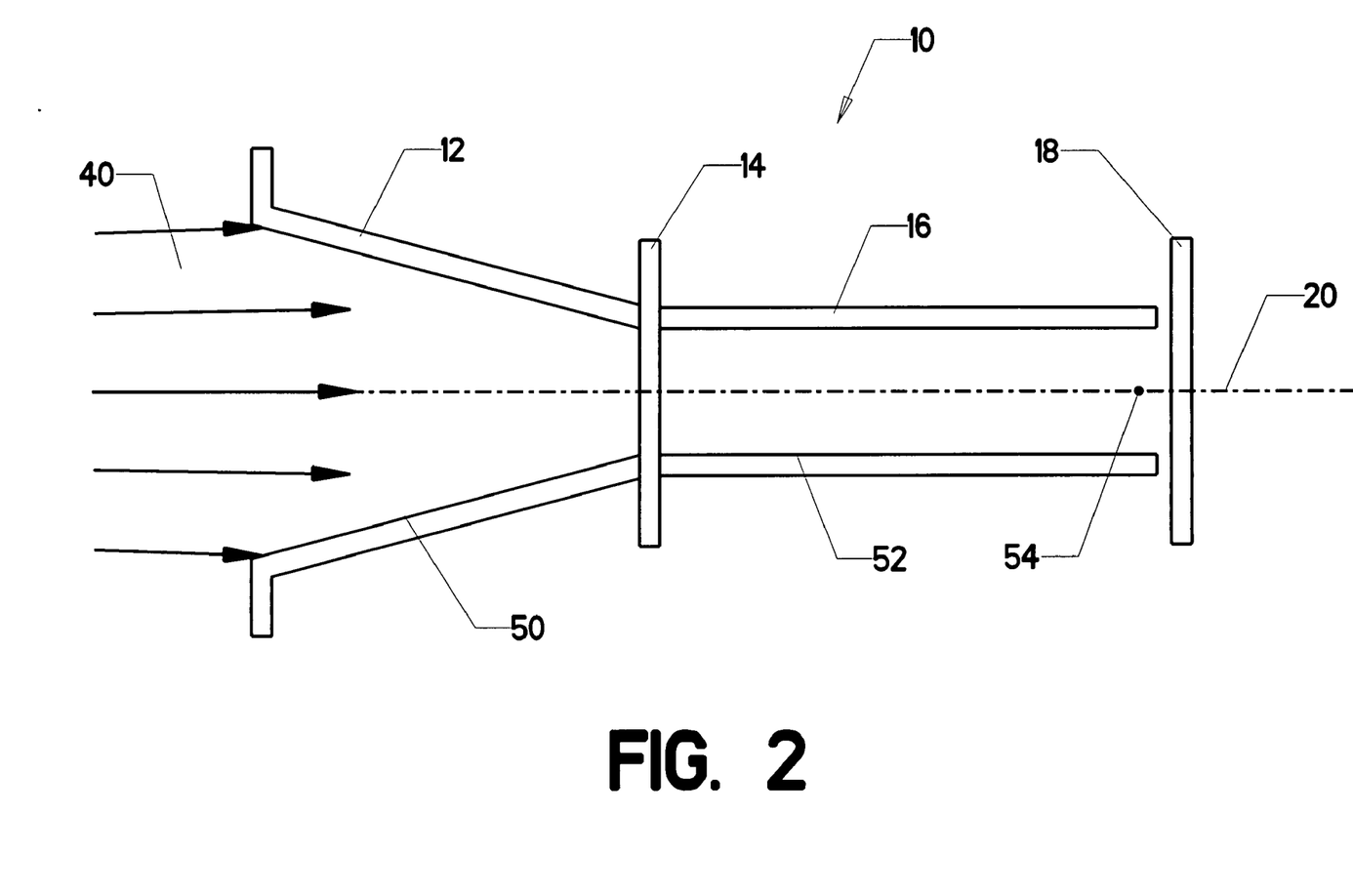
FIG. 2 is an elevation view, showing the X-ray source used in the present invention.

FIG. 2 is a conceptual illustration of the present invention. All the components are radially symmetric about central axis 20. FIG. 2 is actually a cross section of the device taken through the central axis. The angles have been greatly exaggerated for visual clarity, so the reader should not view FIG. 2 as being dimensionally accurate. Electron beam 40 is generated using conventional techniques. It travels from left to right in the orientation shown in the view.

Conical anode 12 receives the electron beam, which is preferably evenly distributed across the anode's internal female conical reflecting surface 50. The conical anode is made of a suitable material for generating X-rays. Molybdenum is a good example of a suitable material. As the electron beam strikes the female conical reflecting surface, X-rays are generated. These will propagate toward the right in the view (toward the smaller diameter part of the female conical reflecting surface).

The X-rays generated then pass into homogenizing optic 16. This component includes an internal cylindrical reflecting surface. The components are sized so that the X-rays generated within the anode preferably reflect at least once off the internal cylindrical reflecting surface before passing out of exit 54.

One or more filters are preferably used. The reader will note that the use of the conical anode—and the fact that the exit is aligned with the center of the electron beam—means that a portion of the electron beam can simply pass unobstructed through the center of the device. First filter 14 is positioned to prevent this. First filter 14 is made from a material which will stop the electron beam. Beryllium is one good example. The first filter can be placed at any convenient location within the device. It is shown in between the anode and the homogenizing optic, but it could be placed to the right of the homogenizing optic and conceivably inside the hollow interior of the anode as well.

Figure 3:
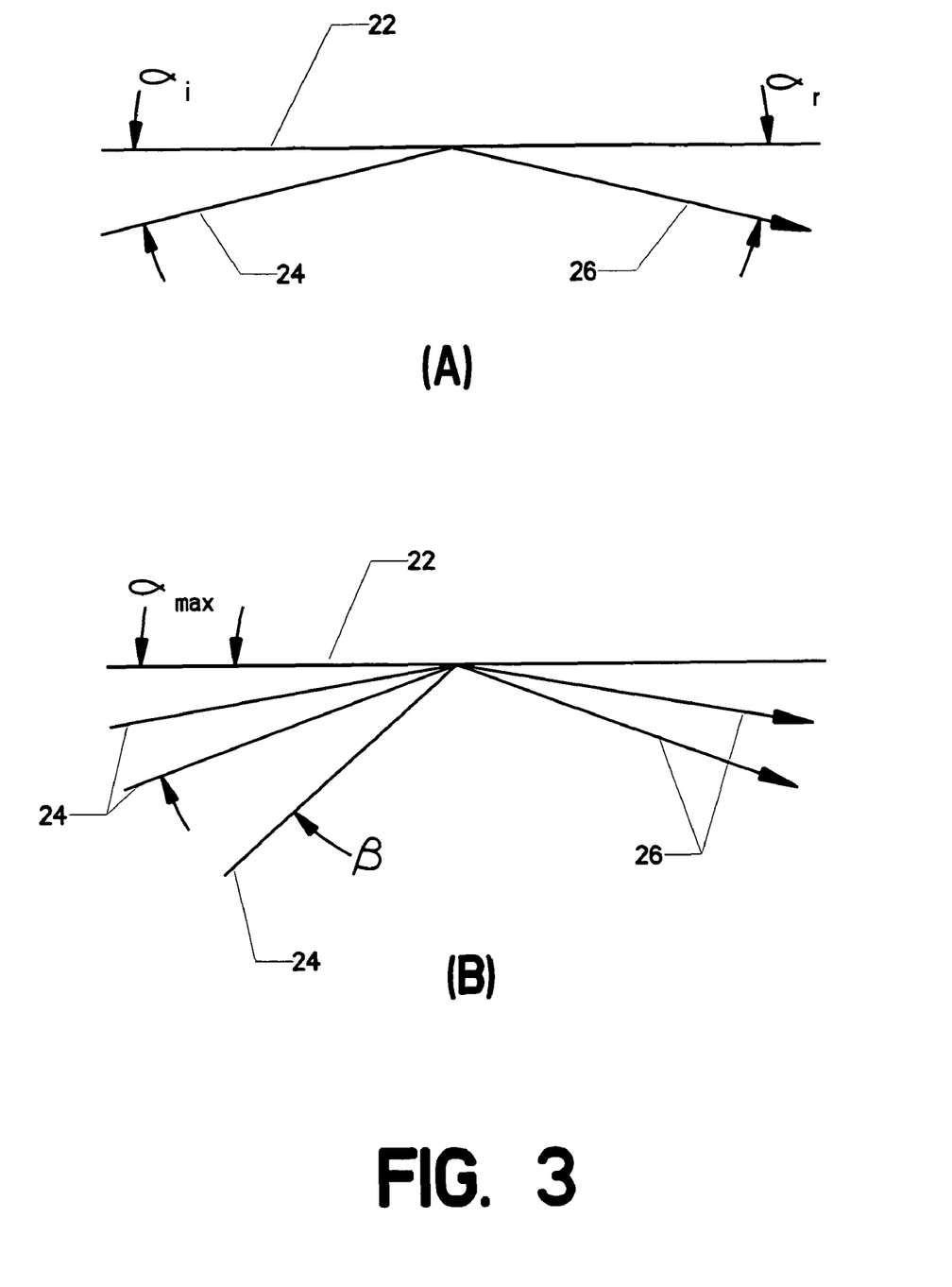
FIG. 3 is a graphical view, showing an incident ray reflecting off a reflecting surface.

Having thus received a general explanation of the components of the present invention, the reader may benefit from an explanation of some of the physical phenomena used to properly size the components. FIG. 3 illustrates the phenomenon of incidence and reflection. In FIG. 3(A), incident ray 24 strikes reflecting surface at angle $\alpha_i$ (the "grazing angle") and is reflected as reflected ray 26 at angle $\alpha_r$. For a reflected ray, these angles are equal.

In the case of an X-ray, the phenomenon of total internal reflection occurs only at very shallow grazing angles. Beyond a maximum grazing angle, the ray will be absorbed and not reflected. The maximum grazing angle is a function of the surface it strikes and the energy of the ray. As an example, the maximum grazing angle for 17.5 KeV X-rays striking a platinum reflecting surface is 0.25 degrees.

FIG. 3(B) illustrates this phenomenon. Incident ray 24 has a maximum grazing angle equal to $\alpha_{max}$. The incident rays striking the reflective surface at or below this grazing angle are reflected. The single ray striking the reflecting surface at a grazing angle beyond the maximum is absorbed and not reflected. Higher energy incident rays tend to have a smaller maximum grazing angle. Thus, by appropriate shaping the X-ray optic, one may ensure that the desired lower energy X-rays are reflected and transmitted, whereas the higher energy X-rays are absorbed.

Figure 4:
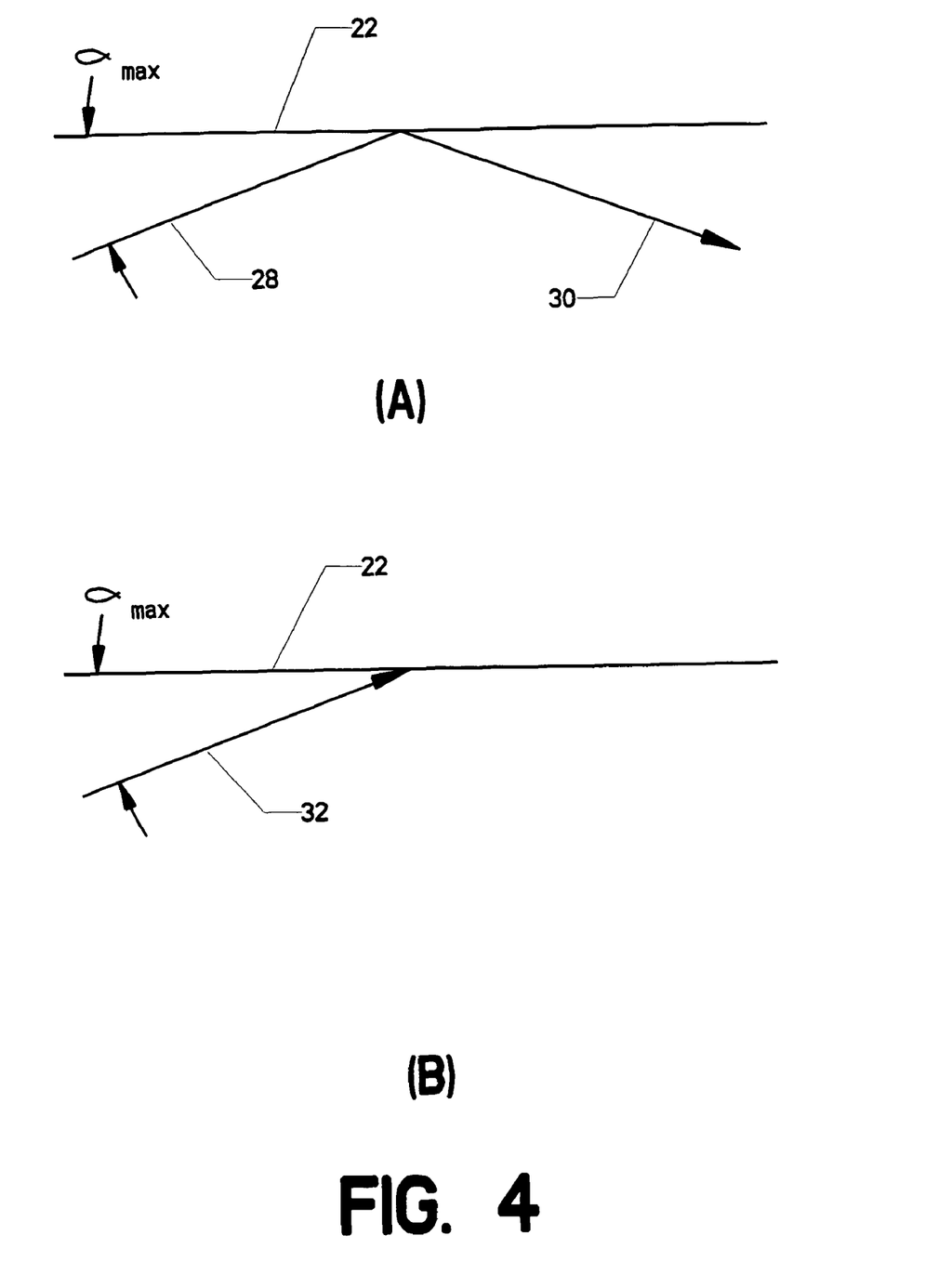
FIG. 4 is a graphical view, showing the reflection of a low energy incident ray versus the absorption of a high energy reflective ray.

FIG. 4 graphically illustrates this phenomenon. In FIG. 4(A), low energy incident ray 28 strikes reflecting surface 22 at the maximum grazing angle for a low energy ray and is reflected as low energy reflected ray 30. In FIG. 4(B), high energy incident ray 32 strikes the reflecting surface at the same angle and is absorbed.

Figure 5:
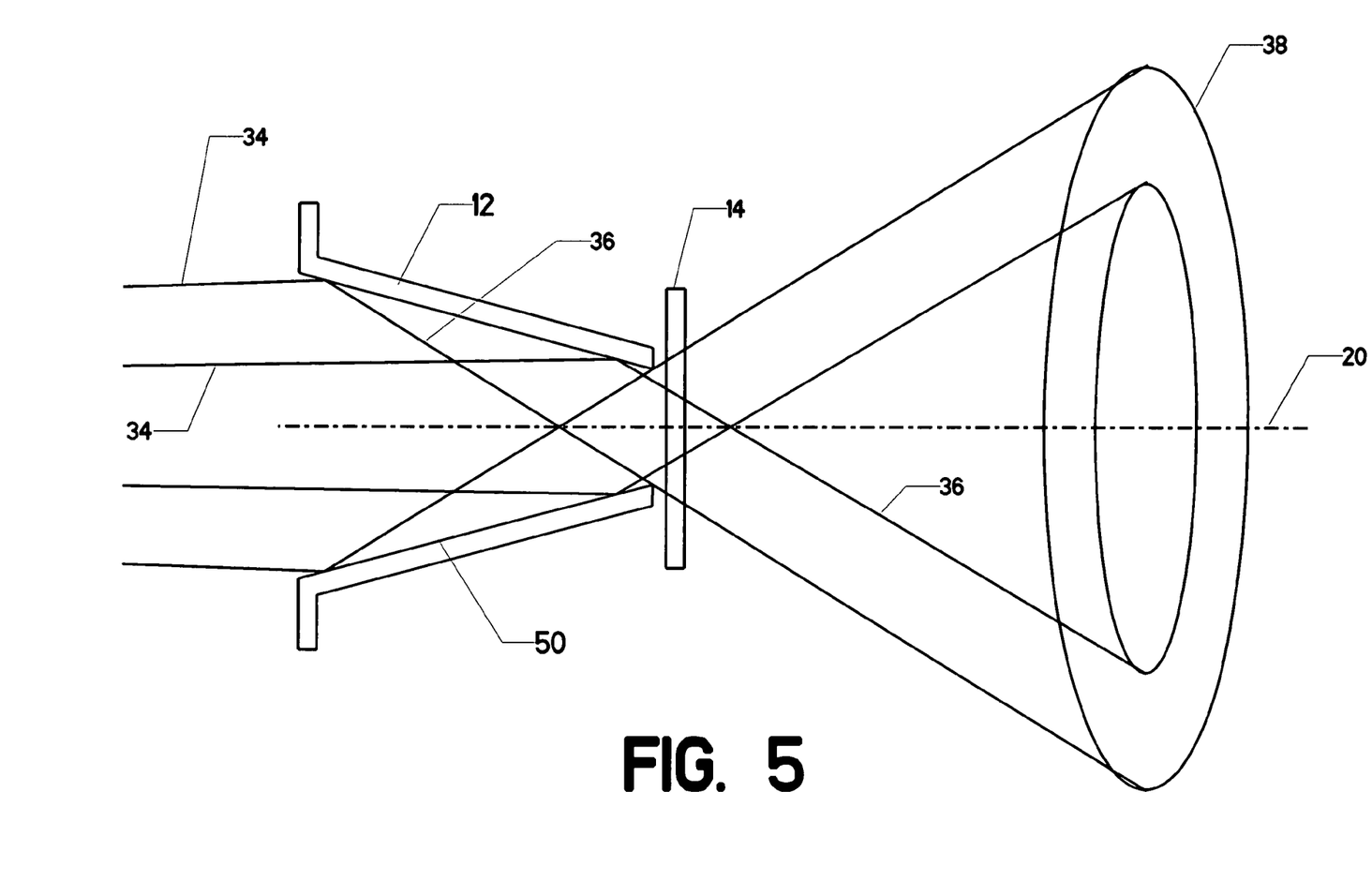
FIG. 5 is an elevation view, showing the creation of a ring projection by the conical anode acting alone.

FIG. 5 shows the operation of the conical anode (without the homogenizing optic). The electron beam is depicted as being comprised of distinct electron rays 34. Two such rays are shown striking the female conical reflecting surface. The upper electron ray strikes the leading portion (from the perspective of the ray's direction of travel) of the conical anode. Reflected X-ray 36 is produced. This is referred to as "reflected" because its angle of departure from the anode surface is equal to the angle of incidence of the electron ray. Of course, the X-ray is not reflected but actually generated at the spot where the electron ray strikes the anode. Those skilled in the art will also realize that the X-ray is not a pure ray but rather a narrow cone centered on the idealized ray depicted.

Nevertheless, visualization as a pure ray helps to convey the "structure" of the X-ray pattern produced. The lower electron ray 34 shown strikes the anode surface at a smaller angle of incidence and the resulting reflected X-ray 36 takes the path shown. The result is the formation of a ring of X-rays at the image plane. Ring projection 38 is actually rotated toward the viewer in FIG. 5 so that its nature may be seen.

The reader will thereby perceive that the X-rays produced by the conical anode are not uniform, and instead are concentrated into a ring pattern. This is undesirable and the homogenizing optic is therefore preferably employed to create a more uniform distribution.

Figure 6:
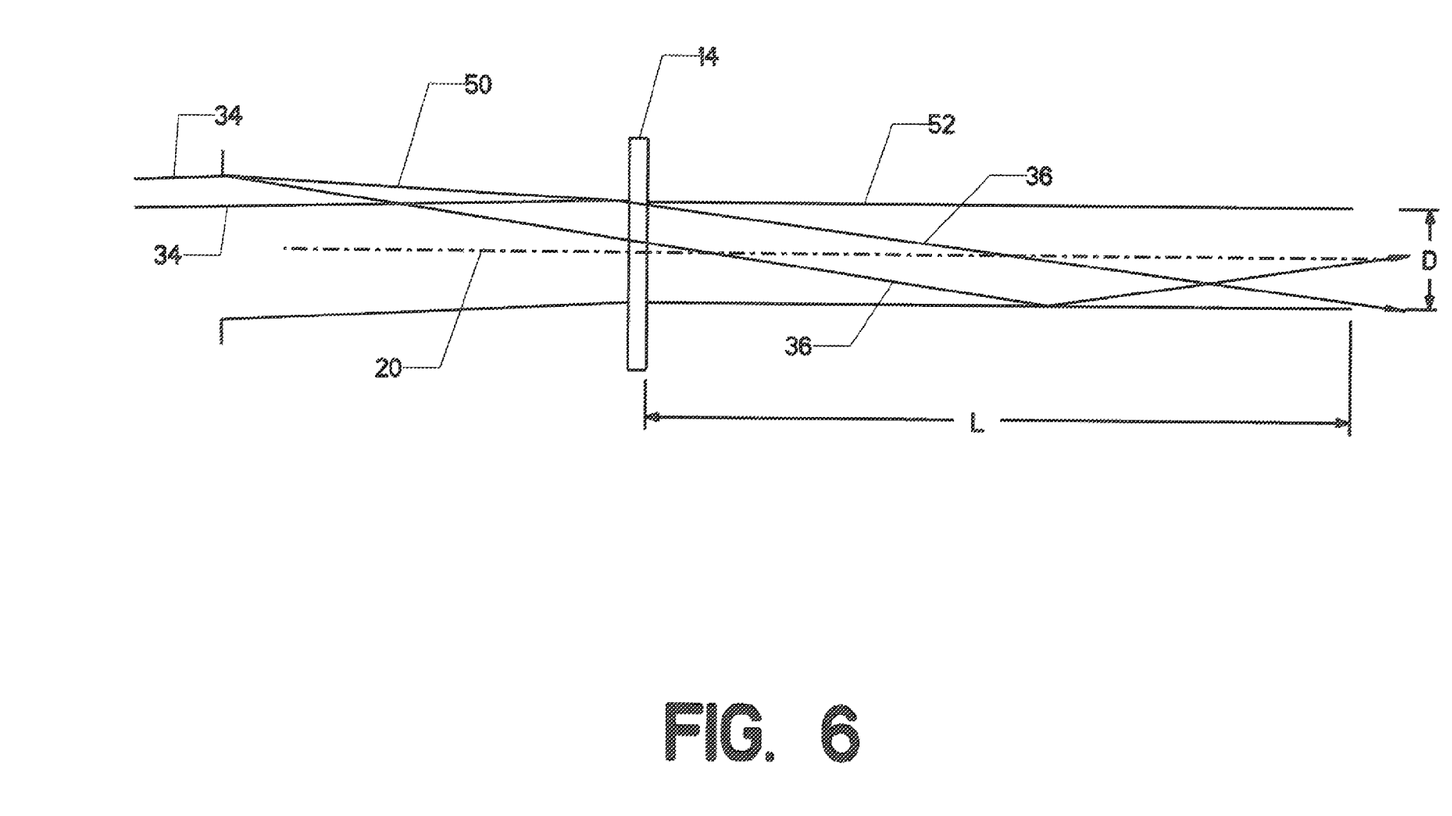
FIG. 6 is an elevation view, showing how the homogenizing optic creates a more uniform emission source.

FIG. 6 shows the geometry of the surfaces involved. Female conical reflecting surface is aligned with central axis 20 and its diameter decreases in the direction of travel of electron ray 34. Its smallest portion is referred to as the exit diameter. Internal cylindrical reflecting surface 52 is also aligned with central axis 20. It has a substantially uniform diameter which is preferably made equal to the exit diameter of the female conical reflecting surface (Those skilled in the art will know that the diameter of the internal cylindrical reflecting surface could be varied while still allowing the device to function). First filter 14 is shown in between the two surfaces, though this need not always be the case.

The angle between the central axis and the female conical reflecting surface is set to produce a desired divergence angle of the X-rays leaving the anode. This will be a function of the materials used in the device and the energy spectrum that is desired to be transmitted. For example, if the internal cylindrical reflecting surface is coated in platinum, and the desired energy is 17.5 KeV (the mammography example), then the desired divergence angle is equal to 0.25 degrees. Again, the reader should note that the angles are greatly exaggerated in the views. The angles used in a practical design of the device are too small to easily visualize.

Since one goal of the present invention is to create an X-ray source with a small apparent spot size, the exit diameter for the conical anode and the internal diameter of the homogenizing optic are preferably quite small. An exit diameter for the conical anode and an internal diameter for the homogenizing optic of about 25 microns is suitable for the mammography application. This becomes the dimension "D" in FIG. 6. The length "L" of the homogenizing optic is set so that at least the more widely diverging X-rays will be reflected at least once within the homogenizing optic (and even more preferably substantially all of the X-rays will be reflected at least once). In this case the length "L" will be no more than one inch.

The homogenizing optic has two purposes. The first is to remove the ring structure in the X-ray beam produced by the conical anode so that the X-rays appear to emanate uniformly from the exit aperture of the optic. The second purpose is to act as a "low pass filter" for removing the high energy X-rays and allowing only the desired lower energy X-rays to pass.

The homogenizing optic reflects X-rays by means of grazing incidence total external reflection. For total external reflection—as mentioned previously—the maximum grazing angle is a very strong function of X-ray energy and reflecting surface material. Higher energy X-rays have a smaller maximum grazing angle for a given reflecting surface. The homogenizing optic is arranged (in combination with the geometry of the conical anode) so that the smallest grazing angle is close to the maximum grazing angle for the desired 17.5 KeV X-rays (The geometry will be altered if another energy level is desired).

Higher energy X-rays will be severely attenuated because they will be absorbed rather than reflected. The homogenizing optic should emit X-rays into a narrow cone (out its second end) with a full cone angle that is twice the maximum grazing angle. The full cone angle will be somewhat increased by scatter from the internal cylindrical reflecting surface due to surface roughness. For this example using the Mo X-rays, the grazing angle is 0.25 degrees so the annular width of the emitted cone is 0.5 degrees. The very small spot size means that a small exit window for an X-ray machine incorporating the invention can be used.

For X-ray energies in this energy region, the best grazing incidence materials are generally high density materials such as tungsten, osmium, tantalum, platinum, and gold. Gold is preferable because it is soft and easier to form into ultra-thin, ultra-smooth coatings. Platinum may also be used.

Those skilled in the art will realize that absorption versus reflection is not an "all or nothing" proposition. As an example, the reflectivity of a platinum surface at a grazing angle of 0.25 degrees is roughly 60% at 17.5 KeV but less than 10% at energies above 23 KeV. An ultra-smooth surface is desirable. "Ultra-smooth" means rms roughness on the order of 10 angstroms or less. For best specular reflection, a surface roughness of about the same size as the X-ray wavelength would be ideal. However, since the X-rays desired have a wavelength of about 0.73 angstroms, this is not possible. A surface roughness of about 5-10 angstroms is possible. This level of roughness will scatter the X-rays into a distribution centered on the direction of specular reflection. The scattering can be somewhat beneficial as it tends to blend and smooth the resulting (cumulative) X-ray beam.

The homogenizing optic is ideally designed to allow X-rays that just graze the female conical reflecting surface of the anode to pass unreflected while all others reflect once at angles up to about 0.3 degrees. This grazing incidence reflection greatly suppresses the high energy X-rays by absorption while reflecting the low energy X-rays very efficiently.

The present system produces a substantial increase in gain compared to conventional anode configurations. That is, the present invention will produce a higher radiance of the desired 17.5 KeV X-rays than a conventional anode. Gain arises from several factors:

1. Although the conical anode does not rotate to enhance heat dissipation, the conical anode surface will be at least ten times as large as the area of the spot on a conventional anode. This allows the application of much more power without overheating the anode;

2. The combination of the conical anode and the homogenizing optic removes all of the high energy continuum so the tube can be operated as higher voltage than a conventional system while maintaining acceptable dose levels. By operating at a higher voltage level, the production of the desired X-ray lines is much more efficient;

3. The conical anode produces gain of the desired line radiation by reabsorbing backscattered electrons, reabsorbing of continuum and conversion into the desired line X-rays, and scattering of the desired line X-rays through the exit diameter; and 4. In some cases, the X-ray optics can produce gain although its primary purpose is to remove the undesired ring structure and remove the high energy continuum.

The optics can be made using any suitable process. One approach is to electroplate the desired reflecting surface onto a highly polished male mold. A thick supporting structure is then added over the electroplated surface. The combined reflecting surface and supporting structure is then released from the male mold.

The present invention has been described with respect to medical applications, but it has applications in other fields as well. Industrial applications often require a narrow spectral band X-ray beam concentrated into a small size. For example, when X-ray fluorescence of an object with dense topography is required, the present invention would be a good choice.

It would also work well for a "stand-off" X-ray illumination system to excite fluorescent X-rays from a small object up to several meters away. Possible applications for such a system would be surveys for weapons materials, automated prospecting systems, and even the analysis of objects in space where close contact is not possible.

The preceding description contains significant detail regarding the novel aspects of the present invention. It should not be construed, however, as limiting the scope of the invention but rather as providing illustrations of the preferred embodiments of the invention. Accordingly, the scope of the invention should be fixed by the following claims, rather than by the examples given.

Having described my invention, I claim:

1. An X-ray emission source for producing a compact and uniform emission of X-rays from an electron beam, comprising:
   a. a conical anode, including a central axis, a female conical reflecting surface having a first end with a relatively large diameter and a second end with a relatively small diameter;
   b. said conical anode being oriented so that said electron beam is centered on said central axis and strikes said female reflecting surface, thereby emitting X-rays out said second end of said conical anode;
   c. a hollow cylinder having an internal cylindrical reflecting surface, a first end, and a second end;
   d. said hollow cylinder being aligned with said central axis;
   e. said first end of said hollow cylinder being located proximate said second end of said conical anode;
   f. a first filter located between said conical anode and said hollow cylinder; and
   g. a second filter located proximate said second end of said hollow cylinder.

2. An X-ray emission source as recited in claim 1, wherein the angle between said female conical reflecting surface and said central axis is about one-half the maximum grazing angle for the desired X-ray energy to be emitted by said X-ray emission source.

3. An X-Ray emission source as recited in claim 1, wherein said first filter is made of beryllium and said second filter is made of aluminum.

4. An X-Ray emission source as recited in claim 1, wherein said conical anode is made of molybdenum.

5. An X-ray emission source as recited in claim 1, wherein the diameter of said internal cylindrical reflecting surface is about equal to said relatively small diameter of said conical anode.

6. An X-ray emission source as recited in claim 1, wherein said hollow cylinder is long enough to reflect all X-rays emanating from said anode at least once.

7. An X-ray emission source for producing a compact and uniform emission of X-rays from an electron beam, comprising:
   a. an electron beam traveling along a central axis;
   b. an anode having a female conical reflecting surface centered on said central axis, said female conical reflecting surface decreasing in diameter in the direction of travel of said electron beam and terminating in an exit diameter from which said X-rays are emitted;
   c. an internal cylindrical reflecting surface having a first end and a second end;
   d. said internal cylindrical reflecting surface being aligned with said central axis, with said first end of said internal cylindrical reflecting surface being located proximate said exit diameter of said female conical reflecting surface;
   e. a first filter located between said exit diameter of said female conical reflecting surface and said first end of said internal cylindrical reflecting surface; and
   g. a second filter located proximate said second end of said internal cylindrical reflecting surface.

8. An X-ray emission source as recited in claim 7, wherein the angle between said female conical reflecting surface and said central axis is about one-half the maximum grazing angle for the desired X-ray energy to be emitted by said X-ray emission source.

9. An X-Ray emission source as recited in claim 8, wherein said first filter is made of beryllium and said second filter is made of aluminum.

10. An X-ray emission source as recited in claim 7, wherein said first filter is made of beryllium and said second filter is made of aluminum.

11. An X-Ray emission source as recited in claim 7, wherein said anode is made of molybdenum.

12. An X-ray emission source as recited in claim 7, wherein the diameter of said internal cylindrical reflecting surface is about equal to said relatively small diameter of said exit diameter of said anode.

13. An X-ray emission source as recited in claim 7, wherein said internal cylindrical reflecting surface is long enough to reflect all X-rays emanating from said anode at least once.

\* \* \* \* \*